(12) United States Patent
Nakanishi et al.

(10) Patent No.: US 9,285,300 B2
(45) Date of Patent: Mar. 15, 2016

(54) MONOLITHIC SILICONE AND METHOD OF SEPARATION, PURIFICATION AND CONCENTRATION THEREWITH

(71) Applicants: Kazuki Nakanishi, Kyoto (JP); Kazuyoshi Kanamori, Kyoto (JP); Gen Hayase, Kyoto (JP); Masahiro Furuno, Saitama (JP); Yoshiyuki Takei, Saitama (JP)

(72) Inventors: Kazuki Nakanishi, Kyoto (JP); Kazuyoshi Kanamori, Kyoto (JP); Gen Hayase, Kyoto (JP); Masahiro Furuno, Saitama (JP); Yoshiyuki Takei, Saitama (JP)

(73) Assignees: GL SCIENCES INCORPORATED (JP); KYOTO UNIVERSITY (JP)

( * ) Notice: Subject to any disclaimer, the term of this patent is extended or adjusted under 35 U.S.C. 154(b) by 270 days.

(21) Appl. No.: 13/629,723

(22) Filed: Sep. 28, 2012

(65) Prior Publication Data

US 2014/0076070 A1    Mar. 20, 2014

(30) Foreign Application Priority Data

Sep. 19, 2012  (JP) ................................. 2012-206388

(51) Int. Cl.

| | | |
|---|---|---|
| *C08G 77/00* | (2006.01) | |
| *C07F 7/02* | (2006.01) | |
| *G01N 1/28* | (2006.01) | |
| *B01J 20/26* | (2006.01) | |
| *B01J 20/291* | (2006.01) | |
| *B01J 20/28* | (2006.01) | |
| *G01N 1/40* | (2006.01) | |

(52) U.S. Cl.
CPC ............... *G01N 1/28* (2013.01); *B01J 20/264* (2013.01); *B01J 20/28042* (2013.01); *B01J 20/28047* (2013.01); *B01J 20/28085* (2013.01); *B01J 20/291* (2013.01); *B01J 2220/86* (2013.01); *G01N 2001/4061* (2013.01)

(58) Field of Classification Search
CPC .................................................... C08J 2383/04
USPC .......................................... 556/400; 521/154
See application file for complete search history.

(56) References Cited

U.S. PATENT DOCUMENTS

| | | | | |
|---|---|---|---|---|
| 5,162,397 A | * | 11/1992 | Descamps et al. ............ 523/219 |
| 2008/0032116 A1 | * | 2/2008 | Hosoya ..................... B01J 20/26 |
| | | | | 428/315.5 |

FOREIGN PATENT DOCUMENTS

| | | |
|---|---|---|
| JP | 7-41374 A | 2/1995 |
| JP | 7-247180 A | 9/1995 |
| WO | 2005110919 | 11/2005 |
| WO | 2007010949 | 1/2007 |
| WO | 2008156199 | 12/2008 |
| WO | 2009096044 | 8/2009 |

OTHER PUBLICATIONS

Bunseki Kagaku, vol. 57, No. 7, pp. 517-529 (2008).
English translation of a portion of page 517 of Bunseki Kagaku, vol. 57, No. 7 (2008).
Bull, Korean Chem. Soc, 2011, vol. 32, No. 10, p. 3603.
Hayase et al., "Synthesis of New Flexible Aerogels from Di- and Trifunctional Organosilanes," Materials Science Research Symposium Proceedings, vol. 1306, Mar. 1, 2011, Cambridge University Press.
SPME (Solid Phase Micro Extraction) using a glass needle coated with a silicone polymer (such as PDMA) as known and is commercially available, http://ir.lib.hiroshimaru.ac.jp/metadb/up/diss/dic_ko5043.pdf, 53 pages, published Sep. 30, 2009.
English translation of a portion of pp. 2 and 3 of SPME (Solid Phase Micro Extraction) using a glass needle coated with a silicone polymer (such as PDMS) as known and is commercially available, http://it.lib.hiroshimaru.ac.jp/metadb/up/diss/disc_ko5043.pdf, 53 pages, published Sep. 30, 2009.

* cited by examiner

*Primary Examiner* — Porfirio Nazario Gonzalez
*Assistant Examiner* — Kofi Adzamli
(74) *Attorney, Agent, or Firm* — Hahn Loeser & Parks LLP

(57) ABSTRACT

The present invention provides a monolithic silicone in the form of an aerogel or a xerogel having flexibility and capable of dissolving molecules of a substance. This silicone monolithic body having continuous through passages is synthesized by copolymerizing starting materials of both a bifunctional alkoxysilane and a trifunctional alkoxysilane or tri- or higher functional alkoxysilanes through a sol-gel reaction for forming a Si—O network while causing phase separation.

20 Claims, 14 Drawing Sheets

MONOLITHIC SILICONE AND METHOD OF SEPARATION, PURIFICATION AND CONCENTRATION THEREWITH

CROSS-REFERENCE TO RELATED APPLICATION

This application is based upon and claims the benefit of priority of the prior Japanese Patent Application No. 2012-206388, filed on Sep. 19, 2012, the entire contents of which are incorporated herein by reference.

BACKGROUND OF THE INVENTION

1. Field of the Invention

The present invention relates to a monolithic silicone that has continuous through pores, is flexible, requires no support and is useful for separation, purification and concentration of a sample or the like, and a treatment method for a sample or the like including separation, purification or concentration.

2. Description of the Related Art

Packing materials and capturing agents utilized in separation, purification and concentration of samples, analytes and the like are broadly classified into three types: packing materials in which stationary liquids such as silicone are immobilized on supports such as a silica gel and diatomite; adsorbent packing materials using activated carbon and zeolite; and polymer packing materials such as phenol resins, acrylate resins and styrene-divinylbenzene copolymers.

A mechanism of separating and concentrating an analyte from a gas phase such as the air by using a stationary liquid type packing material is regarded as gas-liquid partition equilibrium, and a mechanism of separating and concentrating an analyte from an aqueous sample by using this type of packing material is regarded as liquid-liquid partition equilibrium. The corresponding mechanisms working in using an adsorbent packing material are regarded respectively as gas-solid equilibrium (i.e., adsorption equilibrium between a gas phase and a solid phase) and liquid-solid equilibrium. When a polymer packing material is used, an analyte may be adsorbed by the polymer packing material, and it is regarded that mechanisms of both gas-solid equilibrium and gas-liquid equilibrium or both liquid-solid equilibrium and liquid-liquid equilibrium work in this case, but retention in pores of a porous polymer with van der Waals force is dominant in this mechanism and the gas-solid or liquid-solid adsorption equilibrium strongly works.

An adsorbent packing material and a polymer packing material have high mechanical strength in general, and an adsorbent or polymer packing material in a particulate form or recently monolithic form is used to be filled in a column tube. Since spaces between the particles or through pores of the monolith function as passages for a gas or a liquid in such a packing material, there is no need to use a support.

Besides, an absorbent packing material and a polymer packing material have strong retention force and may efficiently retain a volatile substance but are not suitably used for separation, purification and concentration of an unstable substance. Particularly, such a packing material needs large energy for desorbing a substance and many chemical species are denatured at the time of desorption.

Examples of a packing material not using a support are polymer packing materials. The polymer packing materials include phenol packing materials, styrene-divinylbenzene packing materials and the like, and packing materials named as Tenax TA and Porapack (registered trademark) are commercially available respectively as a phenol packing material and a styrene-divinylbenzene packing material. These packing materials are in the form of particles. Other examples of the packing material not using a support are organic polymer monoliths (see "Bunseki Kagaku" vol. 57, No. 7, 517 (2008)). Organic polymer monoliths of acrylamide base, methacrylic ester base and styrene-divinyilbenzene base have been mainly studied and examined, and organic polymer monoliths of styrene base and methacrylic ester base are commercially available.

Such a polymer packing material conducts adsorption (concentration) by capturing, with van der Waals force, target chemical species within pores present on the surface of the polymer. For desorbing the adsorbed chemical species, a method of heating the polymer packing material and purging the chemical species with an inert gas (which method is designated as thermal desorption) is employed in GC analysis. When Tenax TA is used in this manner, dehydration of 2-methylisoborneol may be caused. This is a problem occurring because chemical species to be analyzed (hereinafter referred to as analytes only in the case of chemical species to be analyzed) enter (are adsorbed into) pores present on the surface of the polymer packing material.

When analytes adsorbed by a packing material are to be desorbed with a solvent, the packing material is packed in a vessel for use. Therefore, a space designated as a "bed volume" is formed among particles of the packing material, and hence, a solvent in an amount not only for desorbing the analytes but also for filling the space is excessively required in desorbing the solvent. Since an organic solvent is used also for replacing the bed volume, the concentrated analytes are disadvantageously diluted.

On the other hand, a partition equilibrium type packing material may easily dissolve and desorb analytes in and from a stationary phase and is suitably used for measuring unstable analytes, but it has so weak retention force that a large amount of packing material is necessary for extracting objective analytes from a large amount of matrix. In particular, silicone coated as a stationary liquid for a partition equilibrium type packing material is most frequently used because it is an excellent material stable over a wide temperature range from a low temperature to a high temperature.

A silicone polymer has a property to dissolve analytes like a liquid and may work as a packing material (a stationary liquid) on the basis of a principle of partition equilibrium. Concentration or desorption of analytes on the basis of this principle is free from the problem occurring in a conventional polymer packing material in concentration or desorption of analytes within pores.

In general, polydimethylsiloxane (hereinafter abbreviated as "PDMS") foam is formed into a porous material by mixing a foaming agent with raw materials for forming pores by a gas produced through a chemical reaction. Therefore, the PDMS foam has an ununiform porous structure and pores formed therein are closed, and hence it is impossible to construct a passage penetrating through the structure.

Since the PDMS foam does not have a passage within the structure thereof and does not have a uniform skeleton, it takes time for material transfer between phases (i.e., between a gas phase or a liquid phase and silicone) of analytes, and hence, the PDMS foam is presumed to be poor in extraction efficiency and desorption efficiency.

When analytes concentrated in the PDMS foam are subjected to the thermal desorption to be introduced to gas chromatograph, it also takes time for material transfer. Therefore, a band is spread in introducing a peak sample for the analysis, and it is indispensable to focus a peak band. If a peak band is neglected to focus, a peak shape of a resultant chromatogram is deteriorated, which may lower accuracy in the analysis.

An example of analysis of a food flavor through recovery with a PDMS film has been reported by Dong-Sun Lee (see "Bull. Korean Chem. Soc, 2011, vol. 32, No. 10, 3603). According to this report, a film-shaped PDMS obtained by mixing PDMS in a liquid form and a curing agent is cut into a disc shape to be used as a solid phase extracting material.

The thus produced PDMS film is put in a sample bottle together with a sample and the sample bottle is tightly stoppered. A volatile component volatilized from the sample is solid-phase extracted onto the PDMS film through the partition equilibrium. Thereafter, the PDMS film is taken out, acetonitrile is charged in a microtube as a desorption solvent, and the sampled PDMS film is introduced thereto. The microtube is tightly stoppered, and after stirring for 3 seconds, the PDMS film is taken out of the microtube. One µL of the thus obtained acetonitrile solution is introduced into a GCMS for analysis. Although a recovery factor for the analytes may be increased by increasing the area of the film, it also takes time both for reaching the partition equilibrium and for performing desorption because the PDMS film does not have a passage therein similarly to the PDMS foam.

SPME (Solid Phase Micro Extraction) using a glass needle coated with a silicone polymer (such as PDMS) is known and is commercially available (see http://ir.lib.hiroshimaru.ac.jp/metadb/up/diss/disc_ko504 3.pdf). The amount of silicone used in the SPME is approximately 0.2 mg. This method has a demerit that the amount of silicone polymer used as a stationary liquid is too small to perform highly sensitive analysis. Furthermore, it also takes time both for reaching the partition equilibrium and for performing desorption because the SPME does not have a passage therein similarly to the PDMS foam.

SBSE (Stir Bar Sorptive Extraction) using a magnetic stirrer coated with a silicone polymer (PDMS) is known and is commercially available (see http://ir.lib.hiroshimaru.ac.jp/metadb/up/diss/disc_ko504 3.pdf). The amount of silicone used in this method is several tens times as large as that used in the SPME (specifically, 24 mg). Since the amount of liquid phase is larger than in the SPME, a recovery factor may be remarkably increased. This method has a demerit that the amount of silicone polymer used as a stationary liquid is so large that it takes time for desorbing analytes sorbed through the partition equilibrium. Therefore, when the analytes are to be analyzed by thermal extraction in the GC, it is necessary to perform a band focusing operation using liquid nitrogen or the like, and therefore, productivity in the analysis is degraded.

In this manner, packing materials and capturing agents conventionally used for separation, purification and concentration of samples have problems summarized as follows. The adsorbent packing materials and the polymer packing materials generally have strong retention force and may efficiently retain volatile substances but are not suitably used for separation, purification and concentration of unstable substances. In using these packing materials, energy is necessary particularly for desorption, and many of chemical species are denatured in the desorption.

The partition equilibrium type packing materials, particularly silicone, may not secure passages for a gas or a liquid owing to their properties unless they are immobilized on some support for use. Furthermore, on the basis of a theoretical formula of the partition equilibrium, although the recovery factor from a sample may be improved when a large amount of stationary liquid is used, the amount of packing material that may be immobilized on a support is limited.

When the conventional silicone polymer is used, since it takes time for desorption of analytes, the productivity of the analysis is lowered in the thermal extraction due to a band focusing operation and the like.

SUMMARY OF THE INVENTION

As a result of earnest studies, the present inventors have found a method for producing a monolithic body that has a silicone composition usable as a partition equilibrium type stationary phase, is a self-supporting flexible porous solid usable for separation, purification and concentration without being immobilized on a support, and has continuous through pores with a controlled size.

A monolithic silicone of the present invention is a siloxane polymer having a marshmallow-like solid structure that never loses flexibility even when exposed to liquid nitrogen (with a boiling point of −196° C.) and never decomposes at a high temperature exceeding 320° C. A mechanism of separation, purification and concentration working in this monolithic silicone is dissolution of chemical species in silicone, that is, a skeleton of the monolithic body, by utilizing a difference in a partition coefficient from a matrix. A pharmaceutical or a perfume may be precedently impregnated into a silicone monolithic skeleton to be controlled-released.

The monolithic silicone of the present invention may be applied over a wide range of fields and is applicable not only to pretreatments of a sample conducted in the field of analytical chemistry but also to separation/recovery conducted on an industrial scale. The monolithic silicone of the present invention may be used as a recovery medium for recovering fuel oil or crude oil from seawater at the time of a maritime accident or recovering a perfume or essential oil from citrus fruit or the like by so-called cold pressing. In addition, the monolithic silicone of the present invention has biocompatibility similar to that of a conventional silicone material, and hence is expected to be applied to a postoperative treatment for skin graft or the like by using a controlled-releasing effect of a pharmaceutical.

The mechanism of dissolving and desorbing chemical species in and from the monolithic silicone of the present invention for separation, purification and concentration works similarly in the analytical chemistry field and the life science field treating trace analytes and the field on the industrial scale. Herein, features of the present monolithic silicone will be explained through comparison with conventional materials by mainly describing application examples in the analytic field.

A sol-gel reaction accompanied with phase separation is conventionally known as a method for obtaining a monolithic porous material having continuous through pores with a controlled size in an organic-inorganic hybrid system using an oxide of silica, titania or the like and trifunctional alkoxysilane as starting materials (see Japanese Patent Nos. 2893104 and 3397255). In such a porous body, however, a gel has an extremely low elastic modulus and high brashness as the whole, and hence, it is difficult to provide flexibility resistant to large deformation.

According to the present invention, the sol-gel reaction accompanied with phase separation is conducted by using a starting composition including both a trifunctional alkoxysilane and a bifunctional alkoxysilane, and thus, a monolithic silicone having continuous through pores capable of showing both high flexibility and high porosity that cannot be attained by a conventional material may be produced. In this monolithic silicone, functional groups of hydrocarbon chains or the like directly bonded to silicon not involved in a hydrolysis/ polycondensation reaction are exposed on surfaces of pores, so as to remarkably affect chemical properties of the surfaces of the pores.

Accordingly, in applying the monolithic silicone to separation, purification or concentration, two or more kinds of alkoxysilanes used as the starting materials are appropriately selected, so as to provide chemical properties optimal to a target compound in a controlled manner. The size of the continuous through pores and the volume fraction (the porosity) of the continuous through pores in the whole monolithic silicone are independently and freely controlled respectively in a range of a pore size of 1 to 50 μm and in a range of porosity of 50 to 95% by appropriately selecting the starting compositions.

The present invention provides not only a novel material of a monolithic silicone and a production method for the same but also a method using the monolithic silicone material for overcoming problems occurring in separation, purification and concentration performed by using a liquid silicone stationary phase indispensably requiring a support. The present invention further provides an unprecedented pretreatment method in which consumption of a solvent necessary for desorption may be largely reduced by effectively using flexibility of the monolithic silicone.

Accordingly, the present invention provides A method for producing a monolithic silicone comprising a step of:

copolymerizing silanes of both a bifunctional alkoxysilane and a trifunctional alkoxysilane or tri- or higher functional alkoxysilanes used as starting materials through a sol-gel reaction, whereby forming a Si—O network and causing phase separation, producing an aerogel or a xerogel having continuous through pores and a silicone skeleton capable of dissolving chemical species.

In one aspect of the method for producing a monolithic silicone, one or more of two functional groups of the bifunctional alkoxysilane excluding an alkoxy group may be functional groups selected from the group consisting of a methyl group, a phenyl group, a fluoroalkyl group, a vinyl group and a mercaptopropyl group.

In one aspect of the method for producing a monolithic silicone, the starting materials may include, as a crosslinking agent, an alkoxysilane having a —Si—C—C—Si— structure or a —Si-phenyl-Si— structure for forming the network of the monolithic silicone.

Furthermore, the present invention provides a monolithic silicone, wherein a silicone skeleton of a monolithic body in the form of an aerogel or a xerogel adsorbs chemical species; and in order that continuous through passages allow the chemical species to easily come into contact with the silicone skeleton, and also in order to provide flexibility over a wide temperature range, a bonding form of a Si—O network and sizes of the silicone skeleton and the continuous through pores are controlled.

In one aspect of the monolithic silicone, one or more of two functional groups of the bifunctional alkoxysilane excluding an alkoxy group may be functional groups selected from the group consisting of a methyl group, a phenyl group, a fluoroalkyl group, a vinyl group and a mercaptopropyl group.

In one aspect of the monolithic silicone, an alkoxysilane having a —Si—C—C—Si— structure or a —Si-phenyl-Si— structure may be included in a starting material as a crosslinking agent for forming the network of the monolithic silicone.

In one aspect of the monolithic silicone, the continuous through pores may have a pore size (pore diameter) of 1 to 50 μm and the silicone skeleton may have a skeleton size (diameter) of 1 to 30 μm.

The present invention further provides a sample treatment method using a monolithic silicone of the invention for separation, purification or concentration of a sample.

The present invention still further provides a sample treatment method using a monolithic silicone of the present invention for a pretreatment of a sample to be analyzed.

In one aspect of the sample treatment method, the monolithic silicone may be mechanically expressed for extrusion recovering an extraction solvent retained in the through pores of the monolithic silicone.

In one aspect of the sample treatment method, homogeneous liquid-liquid extraction for extracting analytes or specific chemical species by using a small amount of solvent for a large amount of aqueous sample may be employed for recovering the analytes or the chemical species simultaneously with the extraction solvent by the monolithic silicone.

In another aspect of the sample treatment method, in extracting analytes or specific chemical species by using a small amount of solvent dissolved in water for a large amount of aqueous sample, an emulsion of the solvent including the analytes or the chemical species may be recovered by the monolithic silicone.

Furthermore, the present invention provides an apparatus for treating a sample us comprising a monolithic silicone of the present invention for performing a sample treatment method of the present invention by using the monolithic silicone.

Alternatively, the present invention provides an apparatus for treating a sample comprising a syringe to be charged with a monolithic silicone of the present invention including a solvent; and a plunger that may be inserted into the syringe for expressing the solvent included in the monolithic silicone from the monolithic silicone.

According to the present invention, a monolithic silicone having continuous through pores and capable of showing high flexibility and high porosity that cannot be attained by a conventional material is produced from starting compositions including both a trifunctional alkoxysilane and a bifunctional alkoxysilane.

In this monolithic silicone, functional groups of hydrocarbons or the like directly bonded to silicon not involved in hydrolysis and polycondensation reactions are exposed on surfaces of pores for remarkably affecting chemical properties of the surfaces of the pores, so as to provide chemical properties optimal to a target compound. Thus, the monolithic silicone may be suitably used for separation, purification and concentration without requiring a support and with its flexibility effectively used.

Moreover, in the monolithic silicone of the present invention, analytes may be extremely easily desorbed through an operation of mechanical expression or the like, and hence, a recovery operation may be efficiently performed without spending energy in desorbing the analytes, so as to largely improve productivity in the analysis.

Besides, in the monolithic silicone of the present invention, analytes may be extracted with a small amount of solvent used for a large amount of aqueous sample, or in extracting analytes or chemical species with a small amount of solvent insoluble in water, an emulsion of the solvent may be recovered. Thus, the monolithic silicone may be used over a wide range of application.

DETAILED DESCRIPTION OF THE PREFERRED EMBODIMENTS

Figure 1:
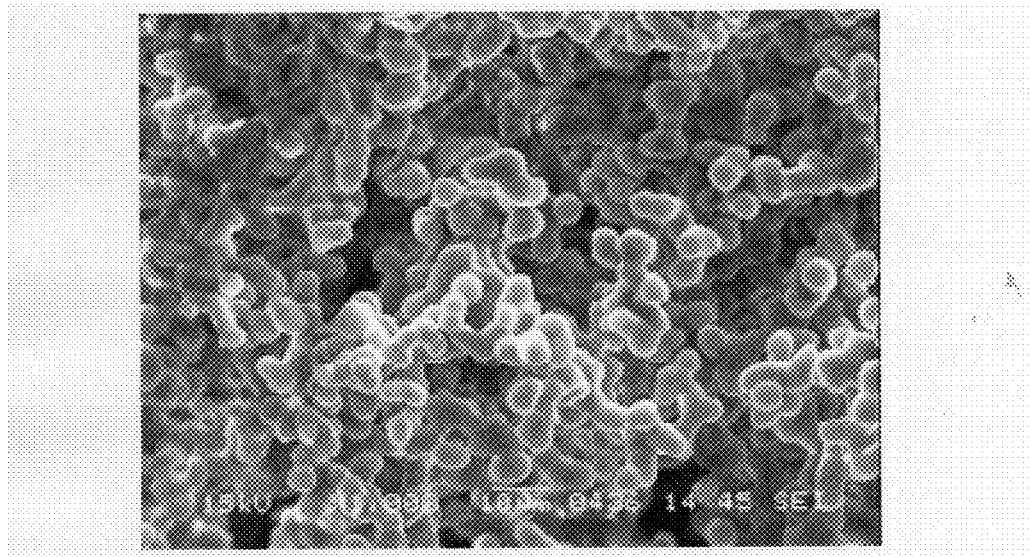
FIG. 1 is an electron micrograph (at 1000× magnification) of a methylated monolithic silicone according to the present invention.

A bifunctional alkoxysilane used for obtaining a monolithic silicone of the present invention is defined as an alkoxysilane having, as four linkage groups of silicone, two alkoxy (—OR) groups involved in polymerization (linkage) and remaining two modification groups not involved in the polymerization. The modification groups are selected in accordance with an intended use of the monolithic silicone, specifically, separation, purification or concentration. Similarly, a trifunctional alkoxysilane used for obtaining the monolithic silicone is defined as an alkoxysilane having three alkoxy (—OR) groups involved in the polymerization (linkage) and remaining one modification group not involved in the polymerization. A tri- or higher alkoxysilane means an alkoxysilane having three or more alkoxy (—OR) groups involved in the polymerization (linkage). Although silicon has four linkage groups, six functional groups may be used when silicon having a —Si—C—C—Si— structure is used, and thus, a denser silicone network may be formed.

Examples of a pretreatment method of the present invention are gas-liquid partition capturing (concentration)-thermal desorption, gas-liquid partition capturing (concentration)-solvent desorption and liquid-liquid partition-solvent desorption (what is called solid phase extraction), and the present monolithic silicone is applicable to any one of them.

As a specific use of the monolithic silicone, an inner wall of a metal capillary or an inner wall of a glass capillary is coated with a thin layer of a monolithic silicone composition, namely, a thin layer of a silicone monolithic body. Such a coating layer is formed by causing, within a capillary, a sol-gel reaction of a starting solution having a monolithic silicone composition by utilizing a known gel coating method for a surface of a micro space through wetting transition. Such a coating layer is used for inactivating the inner surface of a metal capillary column of a gas chromatograph and the coating layer thus applied on the inner surface is characterized in that it never peels off even if the capillary is bent with a small curvature. Some of ultimate forms obtained from materials may not be in the form of a monolith, but these materials through production process of the monolithic silicone have phase separation similar to that caused in forming a monolithic porous structure.

A monolithic silicone porous body, that is, a monolithic body of silicone, formed within a metal, a glass or resin vessel and cut/molded into an appropriate size may be used for separation, purification or concentration process. Since a monolithic silicone porous body has high porosity and is flexible, it may be difficult to fill in a space with specific size and shape after producing it as an independent porous solid. Therefore, a monolithic silicone porous body is precedently formed by injecting a reaction solution into a vessel having a space with the specific size and shape and subjected to a treatment of cleaning, drying, heating or the like if necessary, and the resultant monolithic silicone porous body may be used for separation, concentration or purification process in this state filled in the vessel.

Alternatively, a monolithic silicone porous body, that is, a monolithic body of silicone in which a third particulate component is dispersed may be used. In addition to the trifunctional and bifunctional alkoxysilanes principally included in the monolithic silicone porous body, a third component in the form of fine particles for improving efficiency in the separation, concentration or purification process, such as activated carbon, an oxide, a carbide or a nitride, is dispersed therein. Specifically, as the third component, one of or a mixture of a plurality of substances selected from the group consisting of activated carbon, graphite carbon, carbon nanotube, fullerene, molecular sieves, zeolite, diatomite, a divinylbenzene copolymer, molecular sieve carbon, activated alumina and Florisil may be used.

The present invention relates to an aerogel or a xerogel of a monolithic silicone (having an integral skeleton structure) (as illustrated in FIG. 1) that has continuous through passages with an arbitrary pore size controlled to be suitable to any of the sample treatment methods and has flexibility, and further relates to a use of the porous monolithic silicone not requiring a support. The monolithic silicone is a porous body and is a single structure having continuous through pores of a three-dimensional network.

Figure 3:
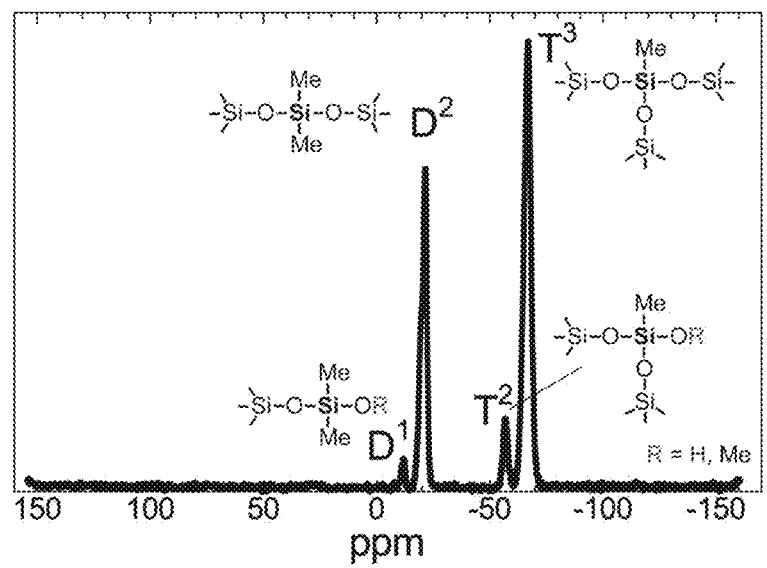
FIG. 3 illustrates a $^{29}$Si CP/MAS solid NMR spectrum of the methylated monolithic silicone of the present invention.
Figure 4:
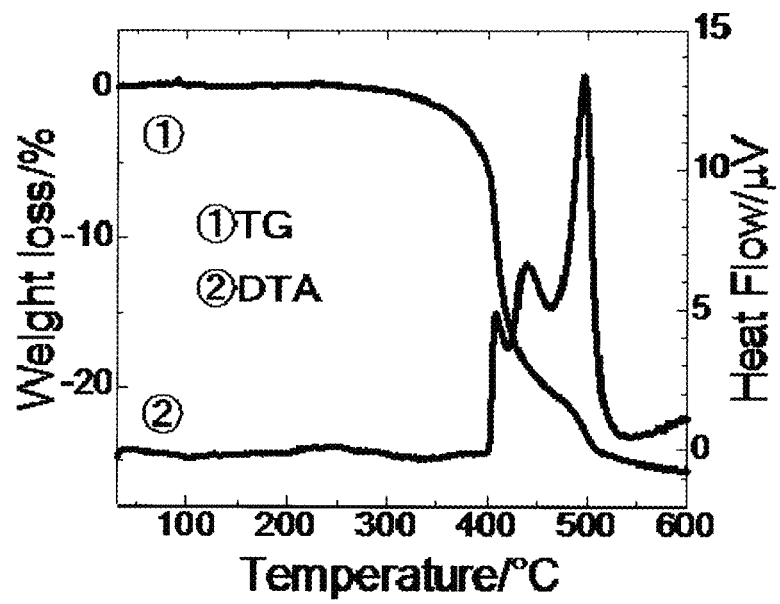
FIG. 4 illustrates thermogravimetric/differential thermal analysis (TG/DTA) curves of the methylated monolithic silicone of the present invention.
Figure 5:
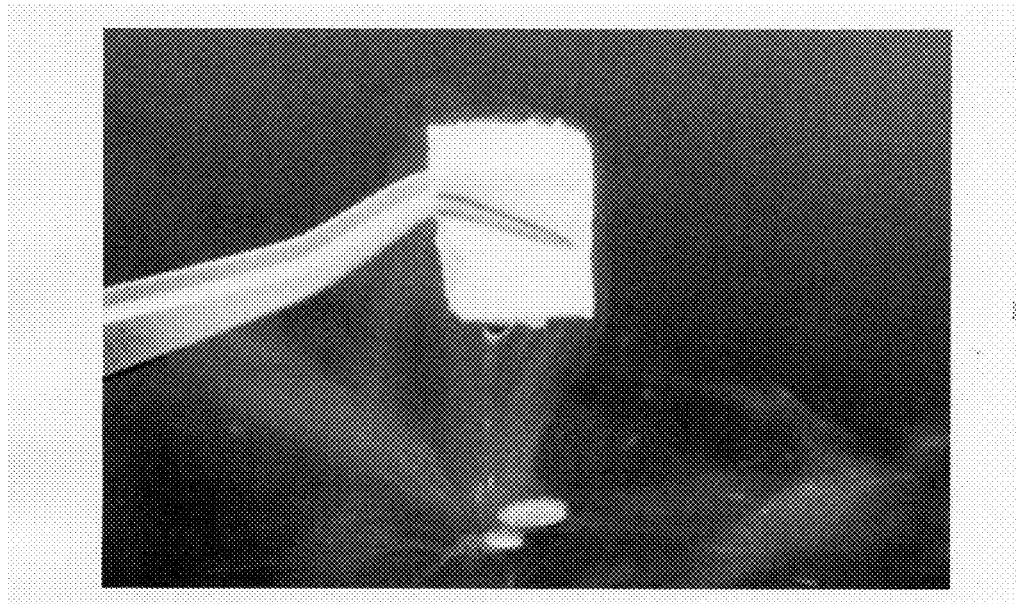
FIG. 5 is a photograph of the methylated monolithic silicone of the present invention impregnated with liquid nitrogen and expressed.

The porous monolithic silicone is synthesized through a sol-gel reaction from starting materials including both a bifunctional alkoxysilane and a trifunctional alkoxysilane or tri- or higher functional alkoxysilanes. Since polymerization is conducted under conditions where silanol groups produced through hydrolysis do not remain in the gel structure if possible, functional groups bonded to the bifunctional and trifunctional alkoxysilanes strongly affect the chemical state of the surface of the monolithic silicone to be produced (see FIG. 3). When a Si—O network is formed through a copolymerization reaction, these starting materials cause phase separation in the presence of a surface active agent, resulting in forming continuous through passages.

The kind of a functional group of alkoxysilane working as a side chain of a Si—O bond after obtaining the structure of the monolithic silicone is not significant for the polymerization reaction but is significant for showing an objective function of the resultant material, and the starting materials and polymerization conditions are controlled for this purpose. The monolithic silicone thus synthesized shows flexibility in a wide temperature range from the temperature of liquid nitrogen (i.e., −195.8° C. under 1 atm.) to 320° C. or more (see FIGS. 4 to 8), is capable of dissolving and desorbing molecules of substances, and requires no support.

Figure 2:
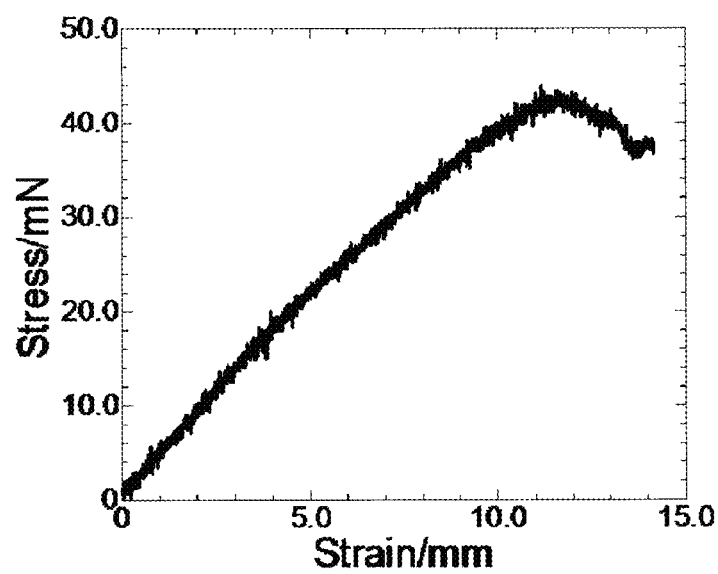
FIG. 2 illustrates a stress-strain curve obtained in a three-point bending test of the methylated monolithic silicone of the present invention using a sample in the shape of a round bar with a diameter of 8 mm, in which linearity is lost in a region with large strain due to local stress concentration to a fulcrum at the center of the sample because of high flexibility.

Foamed silicone is known as a flexible silicone material but its structure is largely different from that of the monolithic silicone of the present invention. In the structure of the foamed silicone, foam is confined by silicone partitions, but the structure of the present monolithic silicone is kept by a skeleton backbone and uniform pores are positively formed therein. The monolithic silicone shows linear elastic response over a wide deformation range in a three-point bending test and has both flexibility and restoring force (see FIG. 2). In this test, a sample in the shape of a round bar with a diameter of 8 mm is used. Since the monolithic silicone has high flexibility, linearity is lost in a region with large strain due to local stress concentration to a fulcrum at the center of the sample. When a monolithic silicone with porosity of approximate 90% is molded into a round or rectangular bar and is subjected to unconfined compression, it may be compressed linearly by approximately 90% and restored completely to the original shape when unloaded. A continuous through structure obtained by uniformly controlled pores forms passages through which molecules of a substance are efficiently retained or desorbed in/from the silicone skeleton. The monolithic silicone of the present invention has porosity of approximately 80% or more.

Furthermore, the present inventors have developed a novel method of applying the present monolithic silicone to various separation, purification and concentration by forming further optimum structures through introduction of various functional groups into the present monolithic silicone in accordance with intended use.

It is indispensable in the structure of the monolithic silicone for conducting optimum analysis to have through pores working as passages and to have a uniform skeleton size as the stationary liquid. It is necessary to optimize sizes of the through pores and the skeleton of the monolithic silicone respectively by gas-liquid partition and liquid-liquid partition. This is because chemical species have different diffusion coefficients in a gas phase and a liquid phase.

The skeleton size (diameter) is determined in consideration of a diffusion rate of analytes in silicone. A silicone monolithic body for gas-liquid partition has a pore size (diameter) of the through pores of 5 to 80 µm and a skeleton size of 0.1 to 500 µm, and a silicone monolithic body for liquid-liquid partition has a pore size of the through pores of 1 to 50 µm and a skeleton size of 1 to 30 µm.

As described above, according to the present invention, a sol-gel reaction using trifunctional and bifunctional alkoxides as precursors is performed, so as to cause an acid-base two-stage reaction based on hydrolysis of an acetic acid catalyst and urea while forming a Si—O network through copolymerization of these starting materials and while controlling phase separation with a surface active agent CTAC (n-hexadecyltrimethylammonium chloride), and thus, a flexible gel is produced. Through combinations of various kinds of precursors under the same synthesis process, various functional groups may be introduced into side chains of siloxanes.

An example of a monolithic body of dimethyl silicone will now be described. In a glass vessel, 15 mL of a 5 mM acetic acid aqueous solution is mixed with 0.8 g of a surface active agent of n-hexadecyltrimethylammonium chloride necessary for the phase separation and 5 g of urea.

Subsequently, 3 mL of methyltrimethoxysilane and 2 mL of dimethyldimethoxysilane are added thereto and a resultant solution is stirred with a stirrer for 30 minutes. This operation starts hydrolysis of alkoxysilane. After stirring, the solution is transferred to a sealed vessel, in which the solution is gelled at 80° C. and simultaneously aged for two days under basic conditions derived from the hydrolysis of urea. The thus obtained wet gel is immersed in a water/isopropyl alcohol (1:1) solution and thereafter washed with isopropyl alcohol for removing an unreacted reagent and the surface active agent.

The wet monolithic gel including isopropyl alcohol obtained by the aforementioned production method is charged in a pressure vessel for replacing the isopropyl alcohol with liquid carbon dioxide, and the resultant is subjected to supercritical drying with a carbon dioxide gas beyond supercritical conditions of carbon dioxide of a temperature of 80° C. and a pressure of 14 MPa, resulting in giving an aerogel. On the other hand, after the wet monolithic gel including isopropyl alcohol obtained by the aforementioned production method is impregnated with normal hexane for replacing the solvent, the resultant is gradually dried at 40° C., resulting in giving a xerogel. Through either drying method, as far as the wet monolithic gel is not dried in extremely short time, a macro porous gel, namely, a monolithic silicone, having equivalent porous structure and porosity may be obtained, and such a monolithic silicone may be suitably used for the purpose of separation, purification and concentration no matter whether it is in the form of a xerogel or an aerogel. An aerogel produced through the supercritical drying may be selected to use merely when a xerogel produced through evaporation drying unavoidably has an extremely high density.

Incidentally, through pores and a skeleton suitable to each pretreatment may be attained by controlling a quantity ratio between a bifunctional alkoxysilane and a trifunctional alkoxysilane and the amounts of a surface active agent and urea.

Figure 6:
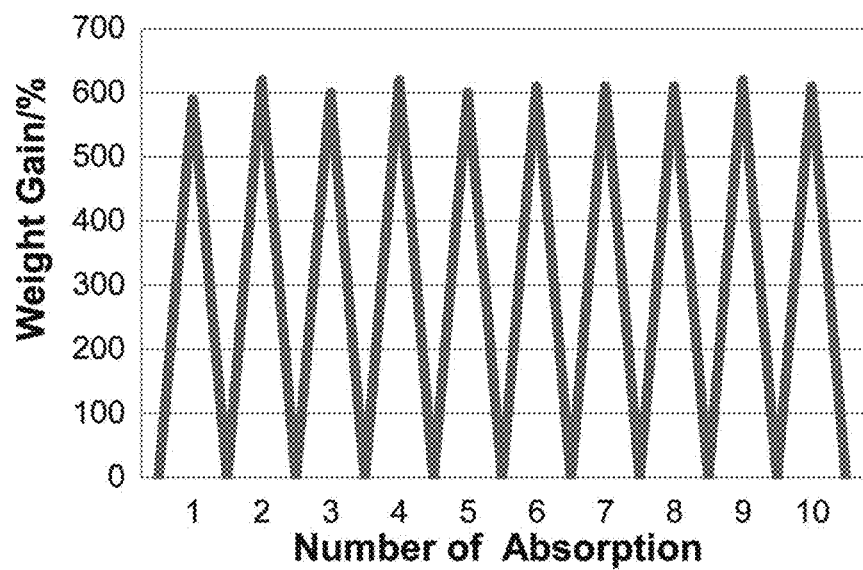
FIG. 6 illustrates a recovery amount and reproducibility obtained as a result of an experiment for recovering n-hexane dispersed in water by using the methylated monolithic silicone.
Figure 7:
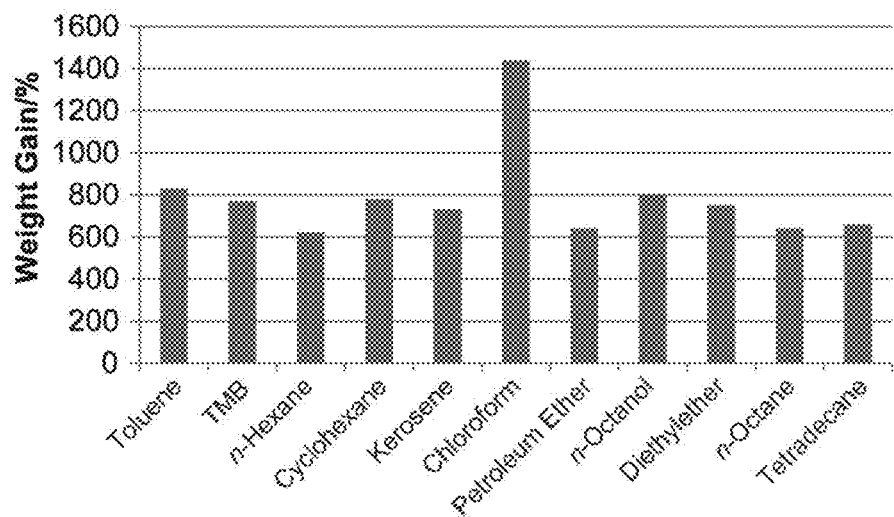
FIG. 7 illustrates a result of an experiment for recovering hydrocarbons dispersed in water by using the methylated monolithic silicone, in which the hydrocarbons are recovered by using a solvent through mechanical expression.
Figure 8:
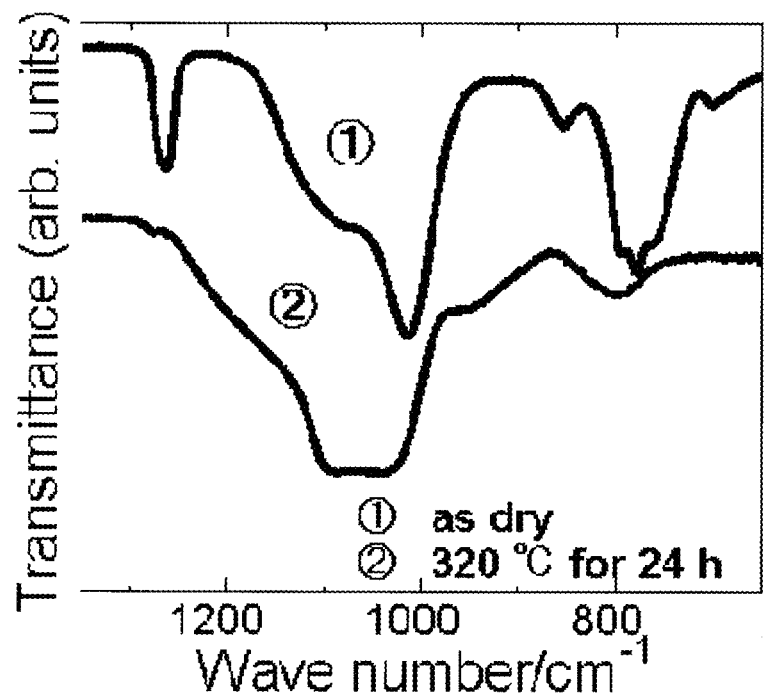
FIG. 8 illustrates infrared absorption spectra of the monolithic silicone obtained after drying and after a heat treatment conducted at 320° C. for 24 hours.

A monolithic body of dimethyl silicone is highly hydrophobic and nonpolar, and hence is suitably used in a sample treatment for a nonpolar analyte such as a volatile toxic substance present in the air or water. FIG. 6 illustrates a result of a recovery experiment for repeating recovery of n-hexane dispersed in water and drying. A dry gel could absorb n-hexane in a weight six times as large as its own weight, and high reproducibility was also exhibited. This monolithic body is free from degradation and may be used repeatedly. FIG. 7 illustrates data obtained by allowing hydrocarbons to be similarly absorbed by the monolithic body to be recovered through mechanical expression by using a solvent. Owing to the solvent retained in pores of the monolithic body, the hydrocarbons may be efficiently recovered. A monolithic silicone having a phenyl group introduced into its side chain is suitably used for a sample treatment for an intermediate polar analyte such as an aromatic compound or a pesticide. A monolithic silicone having a fluoroalkyl group introduced into its side chain is suitably used for capturing a fluorine compound feared to cause health hazard. A monolithic silicone having a vinyl group introduced into its side chain is used for selectively capturing analytes by introducing various functional groups after the production thereof. A monolithic silicone having a mercapto group introduced may be used for capturing thiols and sulfur-containing amino acid by utilizing a S—S bond. Exemplified compositions of starting materials for these monolithic silicones are as follows:

In the production of each of the following exemplified monolithic silicones, 15 mL of a 5 mM acetic acid aqueous solution, 0.8 g of a surface active agent of n-hexadecyltrimethylammonium chloride necessary for phase separation and 5 g of urea are used.

1. An exemplary composition of a fluoroalkylated monolithic silicone is:
   0.0210 mol of methyltrimethoxysilane;
   0.0070 mol of dimethyldimethoxysilane; and
   0.070 mol of 3,3,3-trifluoropropylmethyldimethoxysilane.

Figure 9:
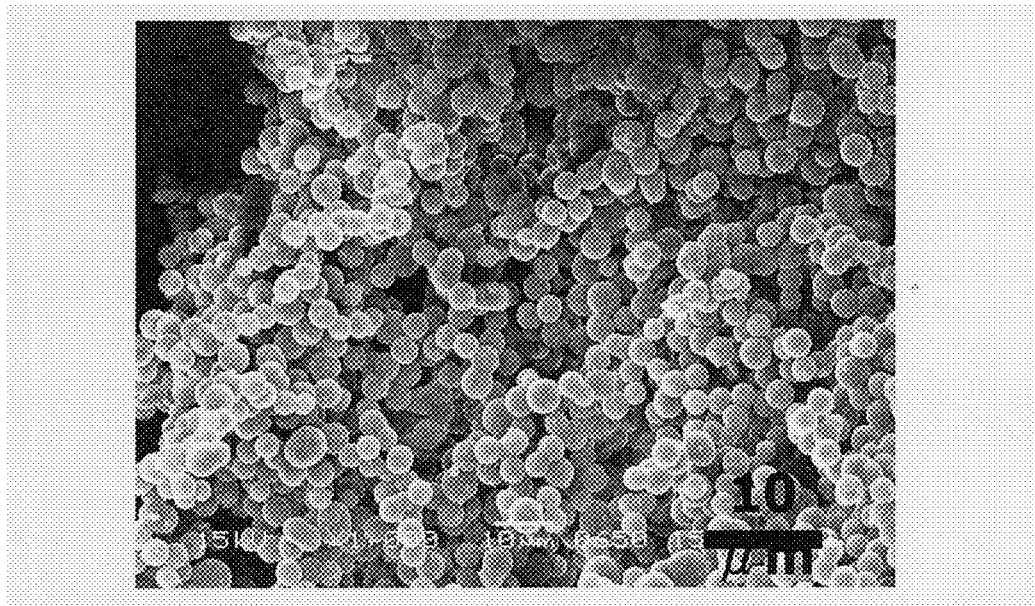
FIG. 9 is an electron micrograph (at 1000× magnification) of a fluoroalkylated monolithic silicone according to the present invention.

FIG. 9 illustrates an electro micrograph (at 1000× magnification) of the fluoroalkylated monolithic silicone obtained by employing the above-described composition.

Figure 10:
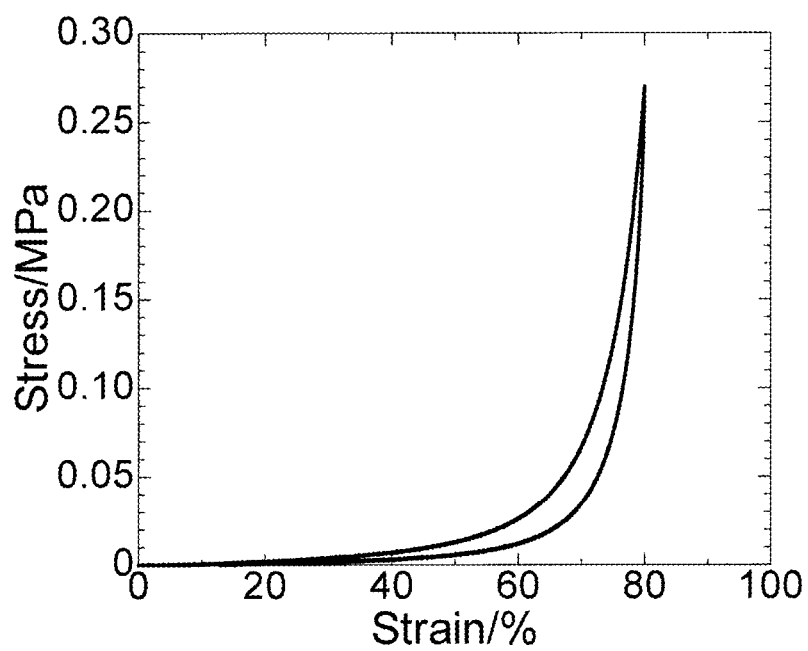
FIG. 10 illustrates a strain curve of the fluoroalkylated monolithic silicone obtained in 80% unconfined compression test.

Besides, a result of a flexibility test for this monolithic silicone is illustrated in FIG. 10. The monolithic silicone showed reversible elastic response, to compressive deformation, to be restored completely to the original shape when unloaded, and has a stress value of approximately 2 MPa or less on a stress-strain curve obtained by 80% unconfined compression, which reveals that the monolithic silicone has flexibility.

2. An exemplary composition of a phenylated monolithic silicone is:
   0.0210 mol of methyltrimethoxysilane;
   0.0070 mol of dimethyldimethoxysilane; and
   0.0070 mol of methylphenyldimethoxysilane.

Figure 11:
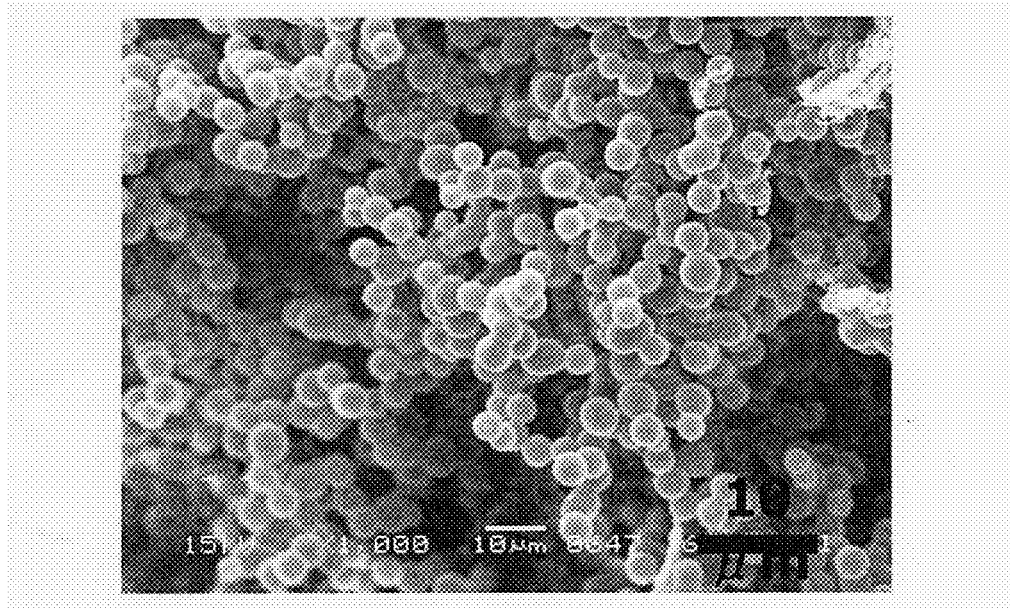
FIG. 11 is an electron micrograph (at 1000× magnification) of a phenylated monolithic silicone according to the present invention.

FIG. 11 illustrates an electro micrograph (at 1000× magnification) of the phenylated monolithic silicone obtained by employing the above-described composition.

Figure 12:
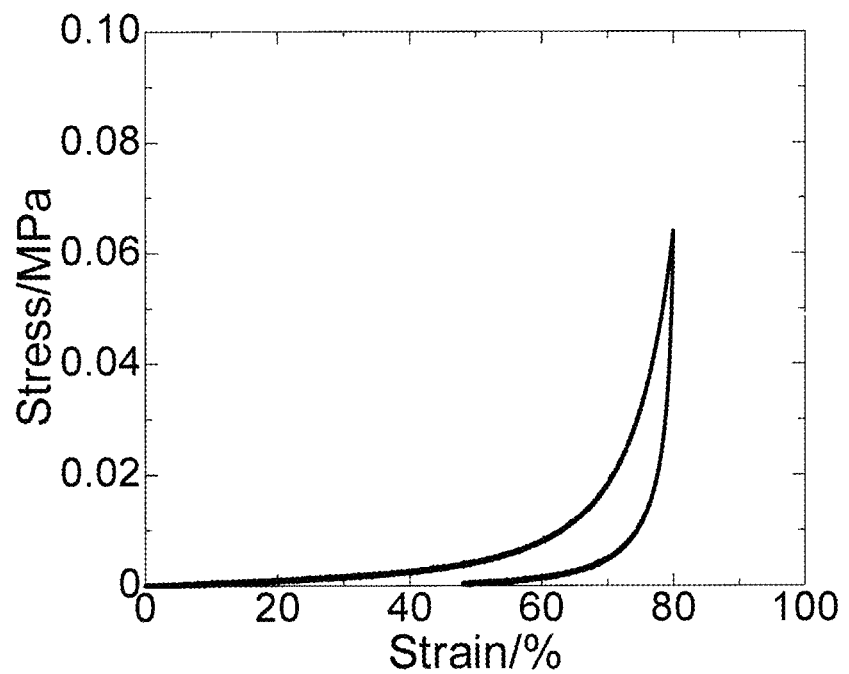
FIG. 12 illustrates a strain curve of the phenylated monolithic silicone obtained in 80% unconfined compression test.

Besides, a result of a flexibility test for this monolithic silicone is illustrated in FIG. 12 as a stress-strain curve obtained by 80% unconfined compression.

3. An exemplary composition of a vinylated monolithic silicone is:
   0.0210 mol of vinyltrimethoxysilane; and
   0.0140 mol of methylvinyldimethoxysilane.

Figure 13:
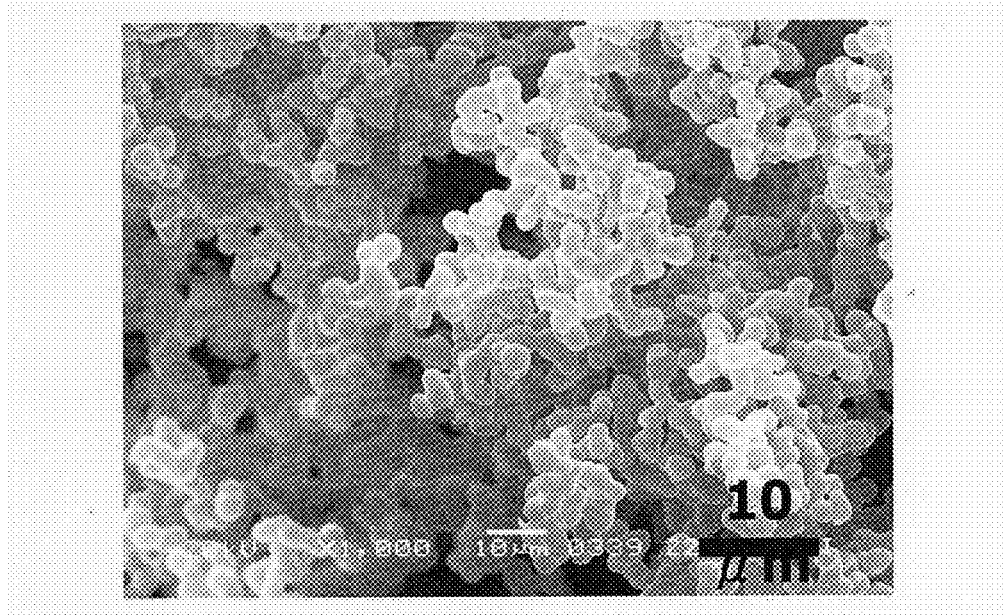
FIG. 13 is an electron micrograph (at 1000× magnification) of a vinylated monolithic silicone according to the present invention.

FIG. 13 illustrates an electro micrograph (at 1000× magnification) of the vinylated monolithic silicone obtained by employing the above-described composition.

Figure 14:
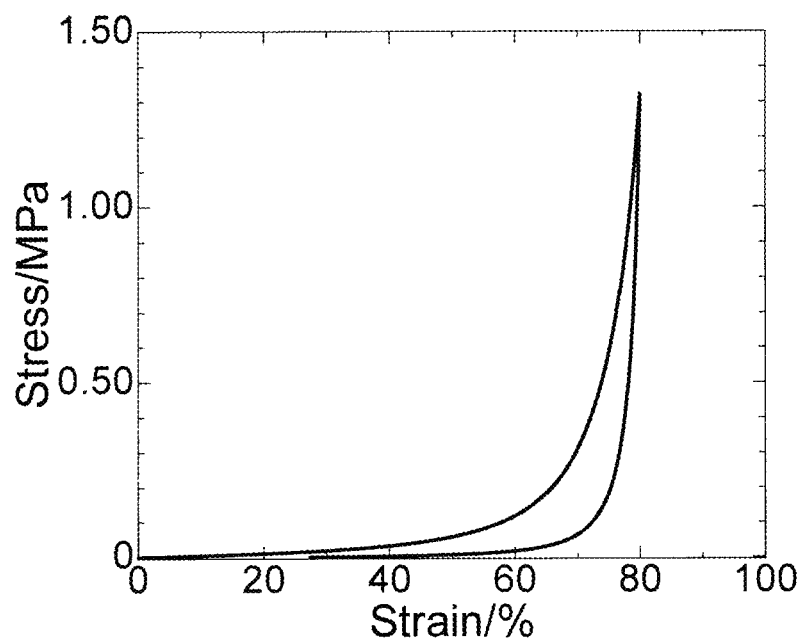
FIG. 14 illustrates a strain curve of the vinylated monolithic silicone obtained in 80% unconfined compression test.

Besides, a result of a flexibility test for this monolithic silicone is illustrated in FIG. 14 as a stress-strain curve obtained by 80% unconfined compression.

4. An exemplary composition of a mercapto-introduced monolithic silicone is:
   0.0210 mol of 3-mercaptopropyltrimethoxysilane; and
   0.0140 mol of 3-mercaptopropylmethyldimethoxysilane.

Figure 15:
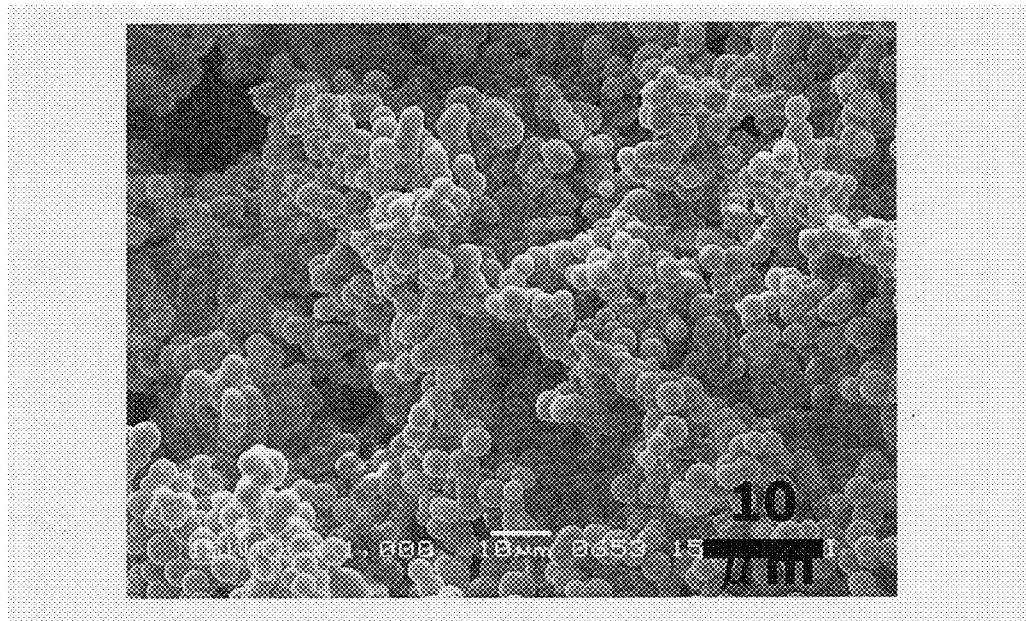
FIG. 15 is an electron micrograph (at 1000× magnification) of a mercapto-introduced monolithic silicone according to the present invention.

FIG. 15 illustrates an electro micrograph (at 1000× magnification) of the mercapto-introduced monolithic silicone obtained by employing the above-described composition.

Figure 16:
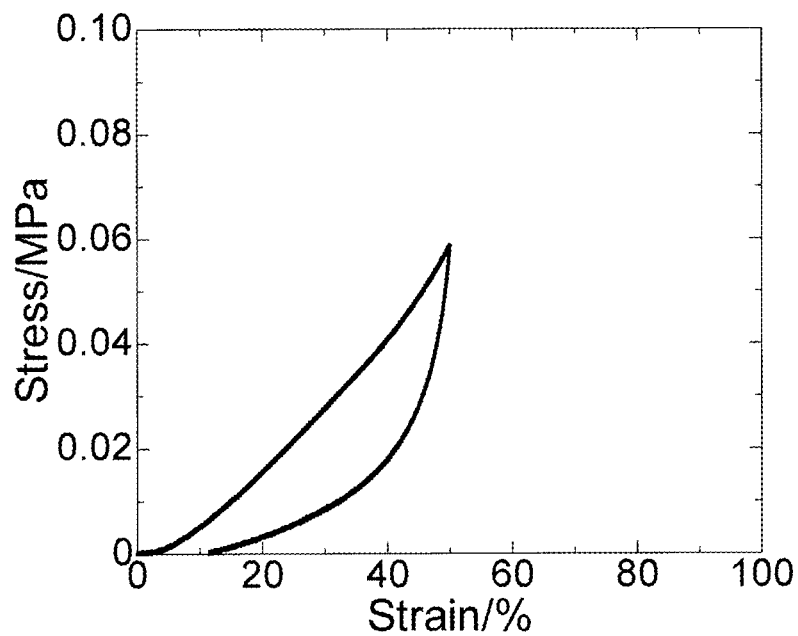
FIG. 16 illustrates a strain curve of the mercapto-introduced monolithic silicone obtained in 50% unconfined compression test.

Besides, a result of a flexibility test for this monolithic silicone is illustrated in FIG. 16 as a stress-strain curve obtained by 50% unconfined compression.

The gel obtained by introducing a mercapto group may stably retain gold fine particles on pore surfaces thereof, and is particularly suitably used for separation, purification and concentration of chemical species having a chemical bond including a sulfur atom such as a disulfide bond.

5. An exemplary composition of a crosslinking bridge group-introduced monolithic silicone is:
   0.0062 mol of 1,2-bis(methyldiethoxysilyl)ethane; and
   0.0140 mol of dimethyldimethoxysilane.

Figure 17:
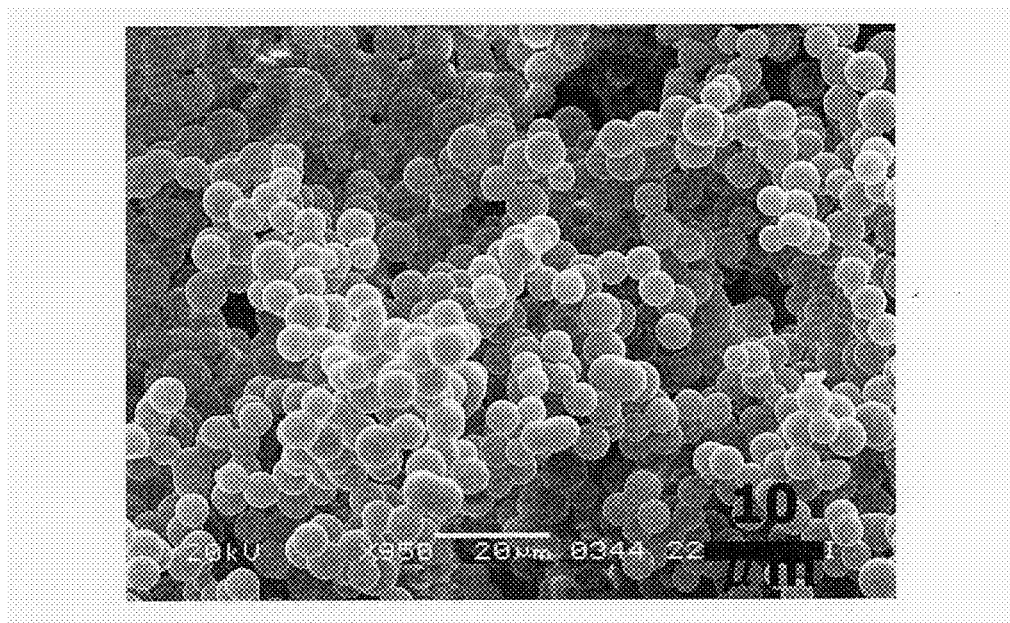
FIG. 17 is an electron micrograph (at 1000× magnification) of a cross-linking bridge group-introduced monolithic silicone according to the present invention.

FIG. 17 illustrates an electro micrograph (at 1000× magnification) of the crosslinking bridge group-introduced monolithic silicone obtained by employing the above-described composition.

Figure 18:
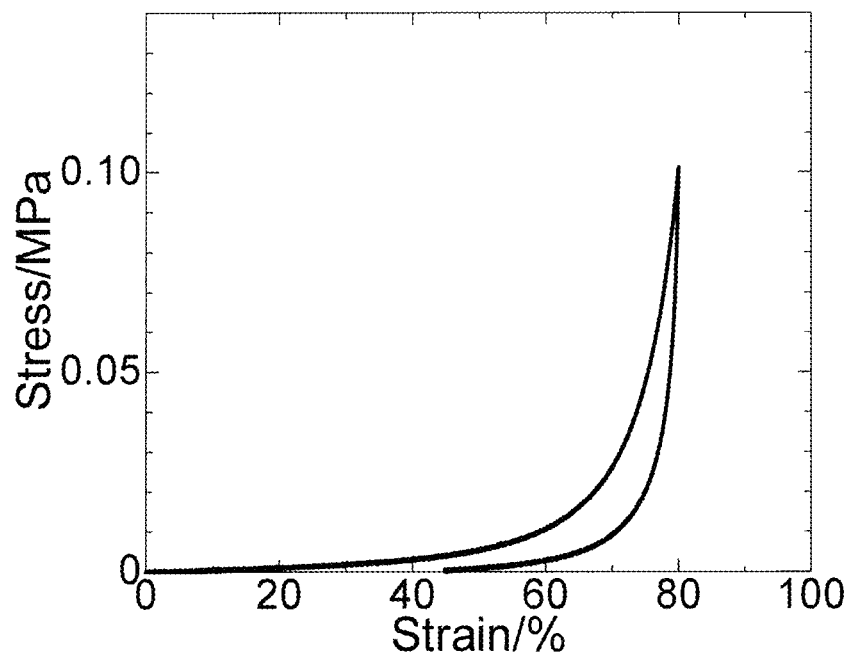
FIG. 18 illustrates a strain curve of the cross-linking bridge group-introduced monolithic silicone obtained in 80% unconfined compression test.

Besides, a result of a flexibility test for this monolithic silicone is illustrated in FIG. 18 as a stress-strain curve obtained by 80% unconfined compression.

Figure 19:
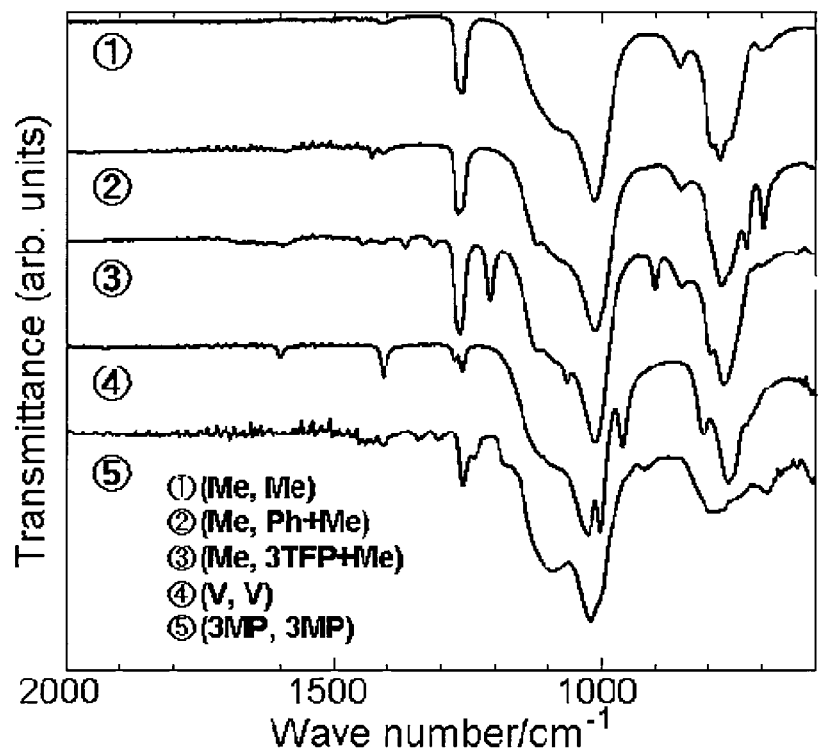
FIG. 19 illustrates infrared absorption spectra of the methylated, fluoroalkylated, phenylated, vinylated and mercapto-introduced monolithic silicones.

FIG. 19 illustrates infrared absorption spectra of monolithic silicones in which a methyl group, a fluoroalkyl group, a phenyl group, a vinyl group and a mercapto group are respectively introduced into functional groups of the bifunctional and trifunctional alkoxysilanes.

Example 1

In a glass vessel, 0.8 g of a surface active agent of n-hexadecyltrimethylammonium chloride necessary for phase separation and 5.0 g of urea were mixed with 15 mL of a 5 mM acetic acid aqueous solution, and 3 mL of methyltrimethoxysilane and 2 mL of dimethyldimethoxysilane were added to the thus obtained mixed solution. After stirring the solution with a stirrer for 30 minutes, the solution was transferred to a sealed vessel and allowed to stand at 80° C. to be gelled. Thereafter, at the same temperature, the thus obtained gel was allowed to stand for 2 days to be aged under basic conditions derived from hydrolysis of urea. The thus obtained wet gel was immersed in a water/isopropyl alcohol (1:1) solution and then washed with isopropyl alcohol, so as to remove an unreacted reagent and the surface active agent. Ultimately, after the isopropyl alcohol used as a solvent was replaced with normal hexane, it was removed through evaporation drying under atmospheric or lower pressure, whereby giving a monolithic silicone (in the form of a xerogel). The monolithic silicone of the present invention, that is, a dimethyl silicone monolithic body thus obtained and having a skeleton size of 5 to 10 μm (hereinafter referred to as the present solid phase material), was subjected to GCMS analysis for 2-methyl-isoborneol (hereinafter referred to as the 2-MIB), that is, a mold smell component, by employing gas-solid adsorption-thermal introduction.

Incidentally, although a monolithic silicone (in the form of a xerogel) is used in this and following examples, since a monolithic silicone (in the form of an aerogel) produced through the production method employing the different drying process has a substantially equivalent porous structure and physical property to the monolithic silicone (in the form of a xerogel) as described above, it is understood that similar effects may be attained by using the monolithic silicone (in the form of an aerogel). It is noted that an aerogel produced through the supercritical drying may be selected to use for pretreatment merely when a xerogel produced through the evaporation drying unavoidably has an extremely high density.

Figure 20:
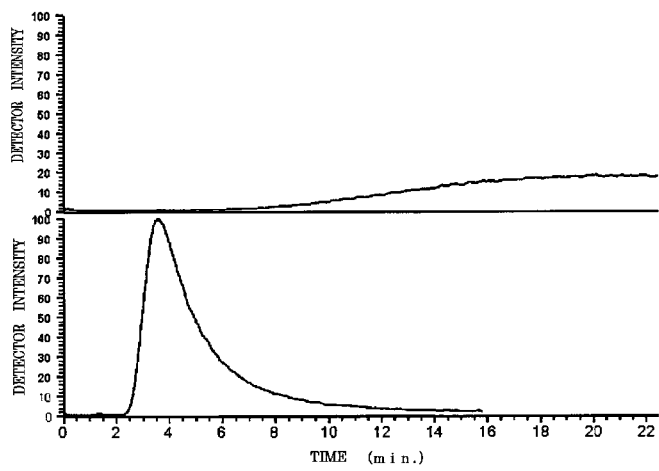
FIG. 20 illustrates a chromatogram in which a breakthrough volume of 2-MIB attained by using the monolithic silicone of the present invention is confirmed.
Figure 21:
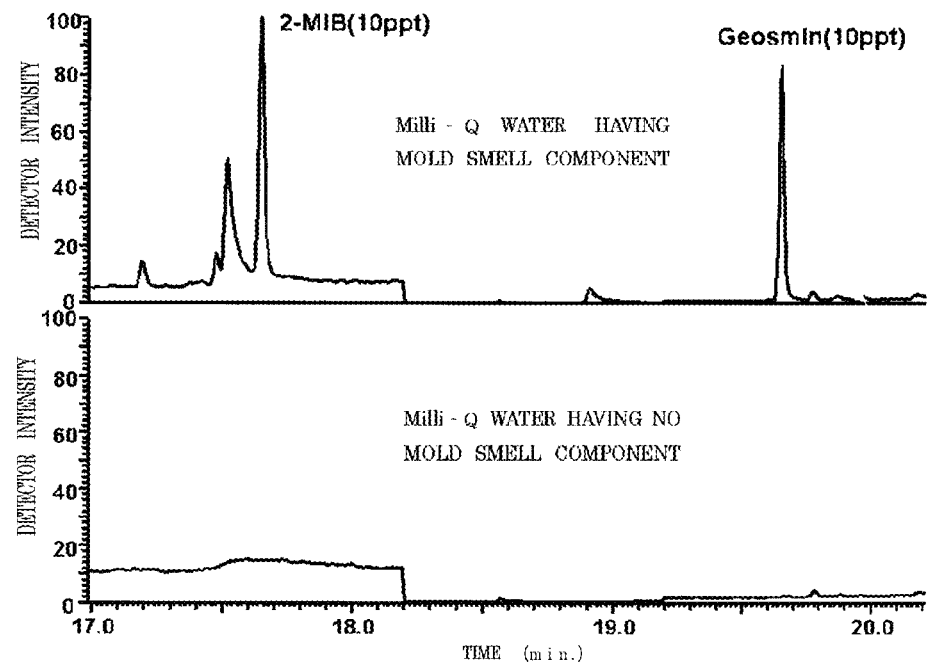
FIG. 21 is a chromatogram of an aquatic mold smell component obtained by using a monolithic silicone of the present invention.

FIG. 20 illustrates chromatograms for confirming breakthrough volumes of the 2-MIB attained with the present solid phase material and Tenax TA used as gas-solid adsorbents, at a sampling temperature of 60° C. and a sampling flow rate of approximately 80 mL/min. As a result of the analysis, it was confirmed that the 2-MIB started to elute after 4.8 minutes in using the present solid phase material and after 2.5 minutes in using Tenax TA.

On the basis of this result, breakthrough volumes of the 2-MIB for these materials were obtained. The breakthrough volume for the present solid phase material was 393.6 mL (82 mL/min.×4.4 min.) and that for Tenax TA was 206.0 mL (82.4 mL/min.×2.5 min.). In this manner, it is revealed that the breakthrough volume for the present solid phase material is slightly less than twice (more accurately 1.9 times) as large as that for Tenax TA, and thus, the present solid phase material shows a higher concentration effect than Tenax TA.

Example 2

A present solid phase material obtained in the same manner as in Example 1 was used for analyzing an aquatic mold smell component (of 2-MIB) by the purge and trap method.
Experiment Conditions:
(1) Conditions for Extracting/Concentrating Mold Smell:
  1. Concentration of sample water: 10 ppt
  2. Extraction temperature for sample water: 60° C.
  3. Flow rate of sample water: 2 mL/min.
  4. Flow rate of purge gas: 80 mL/min.
  5. Extraction time: 2.5 min.
  6. Capturing agent: present solid phase material PDMS (50 mg)
  7. Capturing temperature: 60° C.
(2) GCMS Measurement Conditions (in OPTIC TD Mode)
  1. Temperature for heating capturing tube in introducing sample: 220° C. (5° C./sec.) (retention time: 10 min.)
  2. Analysis column flow rate: 1 mL/min.
  3. Split: 10 mL/min.
  4. GC oven temperature: 40° C. (12 min.)-20° C./min.-250° C. (5 min.)
  6. Capillary column: InertCap 5MS/Sil (0.25 mm I.D×30 m, df=0.25 μm)
  8. SIM mode: 2-MIB (m/z 95, 107), Geosmin (m/z 112, 125)

Example 3

Figure 22:
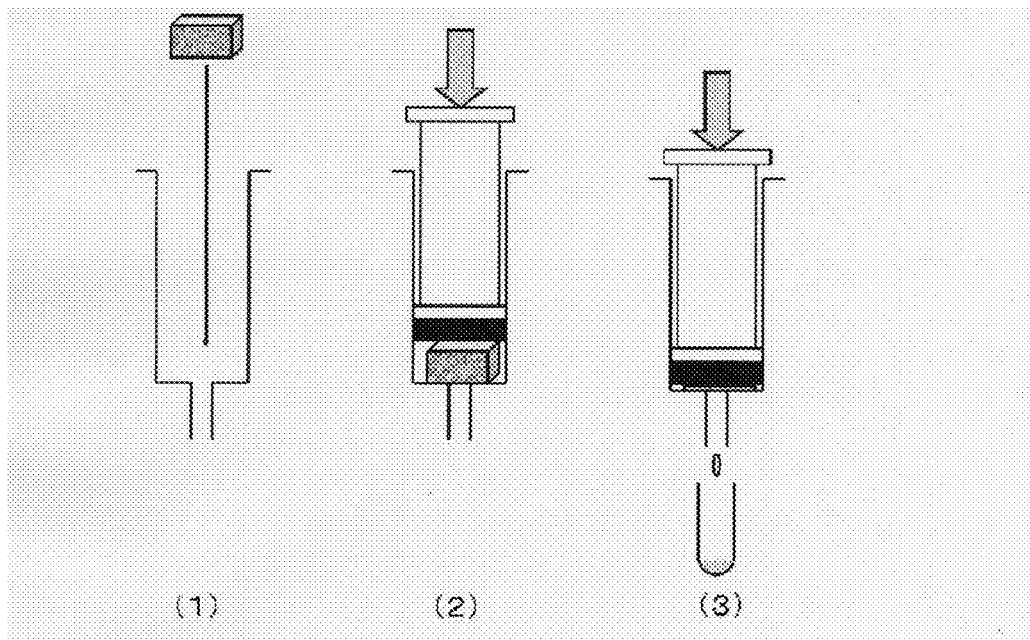
FIG. 22 is an explanatory diagram of an exemplified use of a monolithic silicone of the present invention.

A present solid phase material produced in the same manner as in Example 1 has flexibility, and an organic solvent included (retained) in the present solid phase material may be mechanically expressed. For example, a syringe may be used for expressing an organic solvent from a present solid phase material in the following manner (see FIG. 22).

(1) A present solid phase material including an organic solvent is put in a syringe.
(2) A plunger is inserted into the syringe.
(3) The present solid phase material including the organic solvent is pressed by the plunger so as to express the organic solvent. Since analytes may be thus extracted by using an organic solvent merely in a volume corresponding to a spatial volume, there is no need to perform concentration process as in a conventional method, and the amount of organic solvent to be used is small.

Figure 23:
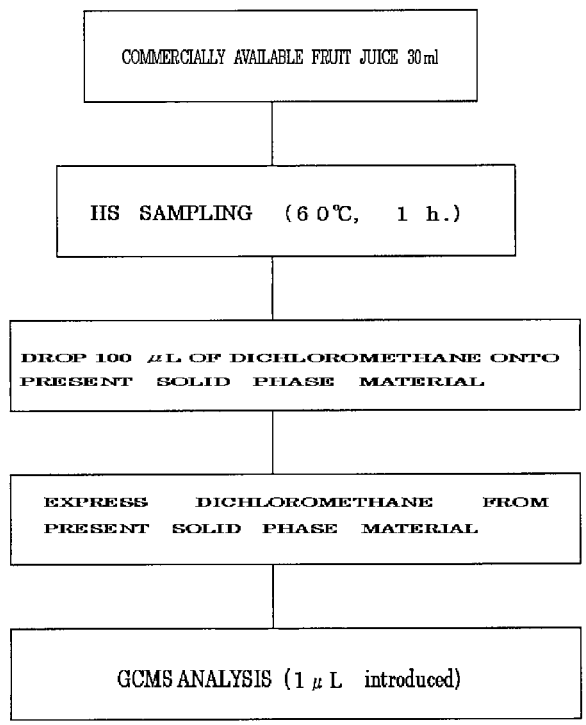
FIG. 23 is a flowchart for analyzing a flavor of commercially available fruit juice by using a monolithic silicone of the present invention.
Figure 24:
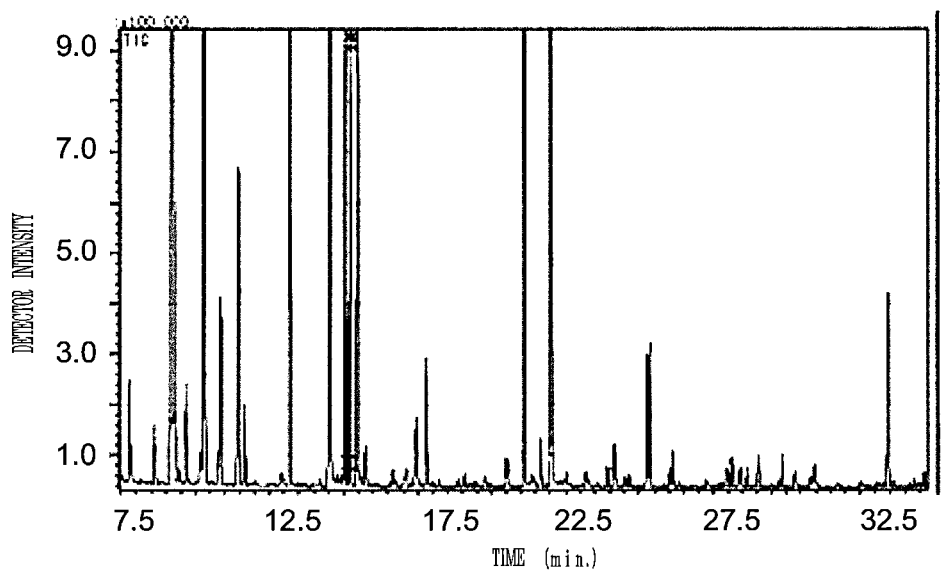
FIG. 24 is a chromatogram illustrating an analysis result of the flavor of the commercially available fruit juice obtained by using the monolithic silicone of the present invention.

A present solid phase material produced in the same manner as in Example 1 was used for analyzing a fragrance component of commercially available fruit juice by employing gas-liquid partition capturing (concentration)-solvent desorption. FIG. 23 illustrates a flowchart of analysis procedures. A headspace vial was charged with 30 mL of commercially available fruit juice, the present solid phase material (in a size of 5 mm×5 mm×5 mm) was placed in a headspace portion, and the juice and the present solid phase material were allowed to stand in this state for 4 hours at a constant temperature of 60° C. The present solid phase material was taken out of the vial, and 100 μL of dichloromethane was dropped onto the present solid phase material. The resultant present solid phase material was put in a syringe for expressing dichloromethane, and 1 μL of dichloromethane thus expressed was introduced as a sample to GCMS. As compared with a conventional solid phase material used for a pretreatment, the consumption of the solvent could be reduced by 1/10. FIG. 24 illustrates a chromatogram obtained as a result of this analysis. The presence of a fragrance component derived from fruit was thus confirmed.
GCMS Analysis Conditions:
  Column: InertCap Pure-WAX (0.25 mm I.D.×30 M, df=0.25 μm)
  Oven temperature program: 40° C. (5 min.)-4° C./min.-250° C. (5 min.)
  Sample introduction: splitless, 1 μl, 250° C.
  MS measurement conditions: EI scan mode (m/z 40-450)

Furthermore, since the present solid phase material has water repellency, there is no need to perform dehydration process using salt cake. Thus, use of a large amount of organic solvent as in a pretreatment performed in using a conventional solid phase material and an artificial operation for concentration process may be avoided, resulting in improving accuracy in the analysis.

Example 4

Figure 25:
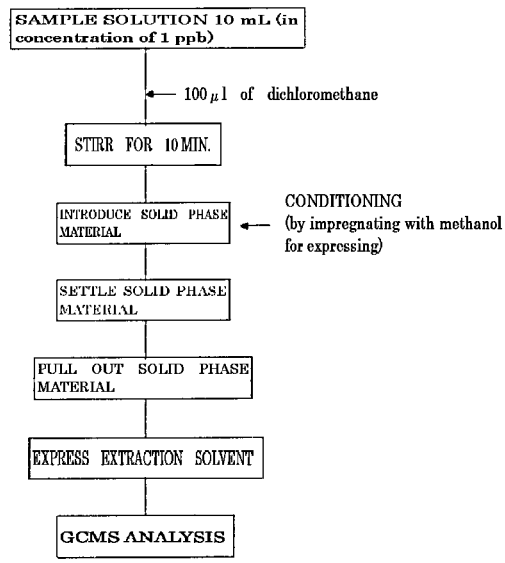
FIG. 25 is a flowchart for analyzing an aquatic pesticide component by using a monolithic silicone of the present invention.
Figure 26:
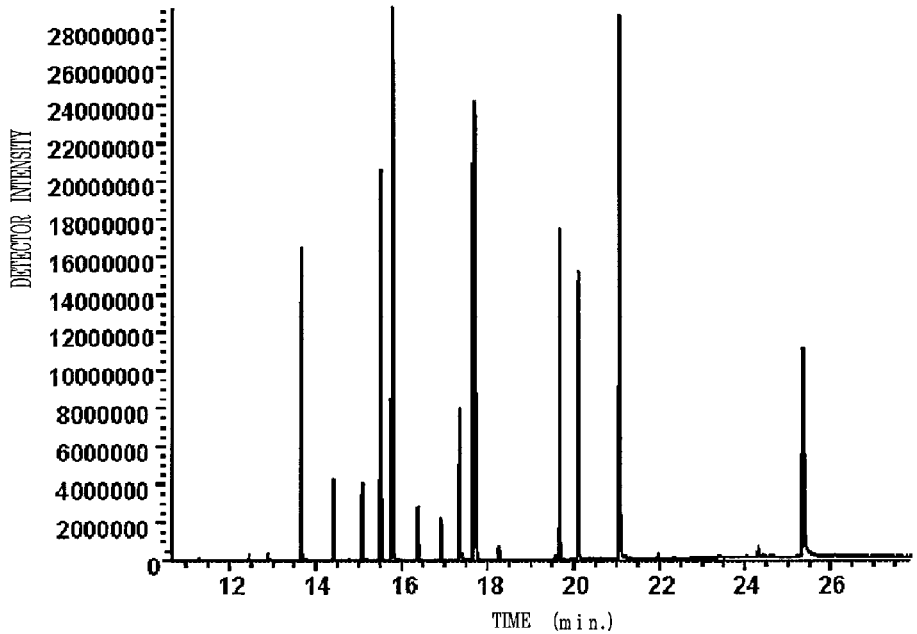
FIG. 26 is a chromatogram of the aquatic pesticide component obtained by using the monolithic silicone of the present invention.

A present solid phase material produced in the same manner as in Example 1 was used for GCMS analysis of an aquatic pesticide by employing liquid-liquid solid phase extraction. FIG. 25 illustrates a flowchart of analysis procedures. The present solid phase material was introduced into a sample solution, and after the present solid phase material settled, the present solid phase material was pulled out of the sample solution. An extraction solvent was expressed from this present solid phase material, and 20 μL of the expressed extraction solvent was introduced to GC in a large amount to be detected by MS. FIG. 26 illustrates a chromatogram thus obtained.

GCMS Analysis Conditions:
Column: InertCap Pesticides (0.25 mm I.D.×30 M)
Retention gap column: 0.53 mm I.D.×1.5 M
Oven temperature program: 62° C. (2 min.)-10° C./min.-280° C. (5 min.)
Conditions for programmed temperature rising at injection port:
(1) Temperature conditions for sample vaporization chamber: An initial temperature of 49° C. was elevated at a temperature increase rate of 5° C./sec. up to 280° C. (5 min.), and cooled to 50° C.
(2) Solvent discharge: flow rate of 50 mL/min. for 30 seconds
(3) Amount of introduced sample: 20 μL
MS measurement conditions: EI scan mode (m/z 45-550)

Figure 27:
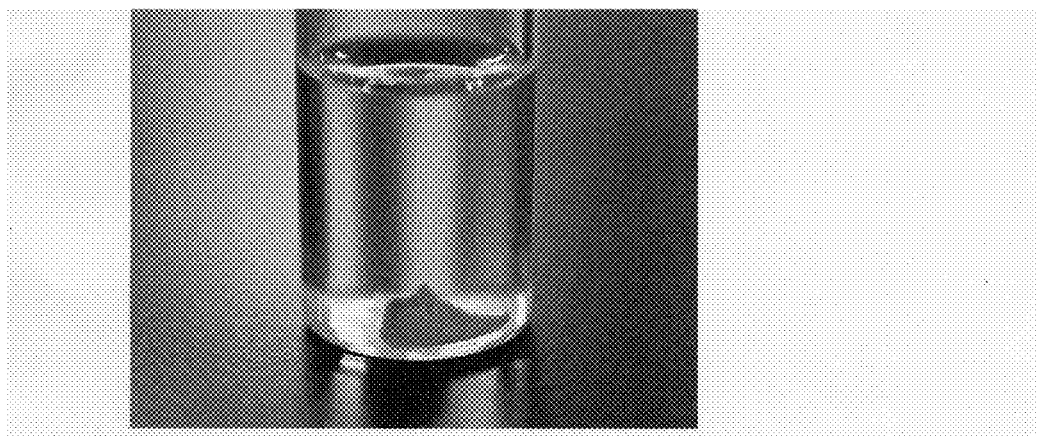
FIG. 27 is a photograph of a mercapto-introduced monolithic silicone of the present invention retaining gold fine particles.

FIG. 27 illustrates a photograph of a mercapto-introduced monolithic silicone of the present invention retaining gold fine particles. A deep red color derived from absorption of gold colloid may be observed in the photograph.

What is claimed is:

1. A monolithic silicone, comprising a continuous silicone skeleton in the form of an aerogel or a xerogel containing continuous through pores,
   the continuous silicone skeleton also comprising a copolymerized silane of both a bifunctional alkoxysilane and a trifunctional alkoxysilane or tri- or higher functional alkoxysilanes, forming a Si—O network,
   wherein one or more of two functional groups of the bifunctional alkoxysilane, other than alkoxy groups, are selected from the group consisting of a phenyl group, a fluoroalkyl group, a vinyl group and a mercaptopropyl group.

2. The monolithic silicone according to claim 1,
   wherein the continuous through pores have a pore diameter of 1 to 50 μm and the silicone skeleton has a diameter of 1 to 30 μm.

3. The monolithic silicone according to claim 2,
   wherein the monolithic silicone exhibits flexibility between a temperature of liquid nitrogen to 320° C.

4. A method for producing a monolithic silicone comprising a step of:
   copolymerizing silanes of both a bifunctional alkoxysilane and a trifunctional alkoxysilane or tri- or higher functional alkoxysilanes used as starting materials through a sol-gel reaction, whereby forming a Si—O network and causing phase separation,
   producing an aerogel or a xerogel having continuous through pores and a silicone skeleton capable of absorbing chemical species,
   wherein one or more of two functional groups of the bifunctional alkoxysilane, other than alkoxy groups, are selected from the group consisting of a phenyl group, a fluoroalkyl group, a vinyl group and a mercaptopropyl group.

5. The method for producing a monolithic silicone according to claim 4,
   wherein the trifunctional alkoxysilane or higher functional alkoxysilanes has 6 functional groups and has a —Si—C—C—Si— or —Si-phenyl-Si— structure for forming the network of the monolithic silicone.

6. The method for producing a monolithic silicone according to claim 4,
   wherein an acid-base two-stage reaction based on hydrolysis of an acetic acid catalyst and urea is performed with the phase separation controlled by a surface active agent.

7. A method for treating a sample, comprising a step of using a monolithic silicone according to claim 1 for a pretreatment of a sample for separation, purification, concentration or analysis.

8. A method for treating a sample, comprising a step of using a monolithic silicone according to claim 2 for a pretreatment of a sample for separation, purification, concentration or analysis.

9. A method for treating a sample according to claim 7, additionally comprising a step of mechanically expressing the monolithic silicone, extruding an extraction solvent retained in the through pores of the monolithic silicone and recovering the extraction solvent.

10. The method for treating a sample according to claim 8, additionally comprising a step of mechanically expressing the monolithic silicone,
    extruding an extraction solvent retained in the through pores of the monolithic silicone, and recovering the extraction solvent.

11. The method for treating a sample according to claim 9, comprising a step of recovering the analytes or the chemical species simultaneously with the extraction solvent by the monolithic silicone, when performing homogeneous liquid-liquid extraction for extracting analytes or specific chemical species by using a small amount of solvent for a large amount of aqueous sample.

12. The method for treating a sample according to claim 10, comprising a step of recovering the analytes or the chemical species simultaneously with the extraction solvent by the monolithic silicone, when performing homogeneous liquid-liquid extraction for extracting analytes or specific chemical species by using a small amount of solvent for a large amount of aqueous sample.

13. The method for treating a sample according to claim 7, comprising a step of recovering an emulsion of the solvent including the analytes or the specific chemical species by the monolithic silicone, when extracting analytes or specific chemical species from a large amount of an aqueous sample with a small amount of solvent insoluble in water.

14. The method for treating a sample according to claim 9, comprising a step of recovering an emulsion of the solvent including the analytes or the specific chemical species by the monolithic silicone, when extracting analytes or specific chemical species from a large amount of an aqueous sample with a small amount of solvent insoluble in water.

15. The method for treating a sample according to claim 10, comprising a step of recovering an emulsion of the solvent including the analytes or the specific chemical species by the monolithic silicone, when extracting analytes or specific chemical species from a large amount of an aqueous sample with a small amount of solvent insoluble in water.

16. An apparatus for treating a sample comprising a monolithic silicone having a continuous silicone skeleton in the form of an aerogel or a xerogel containing continuous through pores,
    the continuous silicone skeleton comprising a copolymerized silane of both a bifunctional alkoxysilane and a trifunctional alkoxysilane or tri- or higher functional alkoxysilanes forming a Si—O network,
    wherein at least two functional groups of the bifunctional alkoxysilane, other than an alkoxy groups, are selected from the group consisting of a phenyl group, a fluoroalkyl group, a vinyl group and a mercaptopropyl group, for performing a method for treating a sample according to claim 7 by using the monolithic silicone.

17. An apparatus for treating a sample comprising a monolithic silicone according to claim 16, wherein the monolithic silicone contains continuous through pores having a pore diameter of 1 to 50 μm and a silicone skeleton having a diameter of 1 to 30 μm.

18. An apparatus for treating a sample according to claim 16, further comprising:
 a syringe to be charged with the monolithic silicone including a solvent; and
 a plunger that may be inserted into the syringe for expressing the solvent included in the monolithic silicone from the monolithic silicone.

19. The sample treater according to claim 17, further comprising:
 a syringe to be charged with the monolithic silicone including a solvent; and
 a plunger that may be inserted into the syringe for expressing the solvent included in the monolithic silicone from the monolithic silicone.

20. The monolithic silicone according to claim 1, wherein the trifunctional alkoxysilane or higher functional alkoxysilanes has 6 functional groups and has a —Si—C—C—Si— or —Si-phenyl-Si— structure.

* * * * *